(12) United States Patent
Walker et al.

(10) Patent No.: US 6,450,990 B1
(45) Date of Patent: Sep. 17, 2002

(54) CATHETER WITH MULTIPLE HEATING/COOLING FIBERS EMPLOYING FIBER SPREADING FEATURES

(75) Inventors: Blair D. Walker, Lake Forest, CA (US); Scott M. Evans, Santa Ana, CA (US); David P. Balding, Mission Viejo, CA (US); Gregg Hallam, Foothill Ranch, CA (US); Lynn M. Shimada, Orange, CA (US)

(73) Assignee: Alsius Corporation, Irvine, CA (US)

( * ) Notice: Subject to any disclaimer, the term of this patent is extended or adjusted under 35 U.S.C. 154(b) by 0 days.

(21) Appl. No.: 09/294,080

(22) Filed: Apr. 19, 1999

Related U.S. Application Data (63) Continuation-in-part of application No. 09/133,813, filed on Aug. 13, 1998.

(51) Int. Cl.$^7$ .................................................. A61F 7/12
(52) U.S. Cl. ...................... 604/113; 604/96.01; 604/291
(58) Field of Search ............................... 604/26, 28, 43, 604/500, 6.13, 4.01, 22, 96.01, 113, 290, 291; 606/20–23

(56) References Cited

U.S. PATENT DOCUMENTS

| | | |
|---|---|---|
| 2,058,780 A | 10/1936 | Elliott |
| 2,077,453 A | 4/1937 | Albright |
| 2,308,484 A | 1/1943 | Auzin et al. |
| 3,125,096 A | 3/1964 | Antiles et al. |
| 3,142,158 A | 7/1964 | Podolsky |
| 3,238,944 A | 3/1966 | Hirschhorn |
| 3,282,267 A | 11/1966 | Eidus |
| 3,327,713 A | 6/1967 | Eidus |
| 3,425,419 A | 2/1969 | Dato |
| 3,504,674 A | 4/1970 | Swenson et al. |
| 3,738,372 A | 6/1973 | Shioshvili |

(List continued on next page.)

FOREIGN PATENT DOCUMENTS

| | | |
|---|---|---|
| WO | WO 98/26831 | 6/1998 |
| WO | WO 98/31312 | 7/1998 |

*Primary Examiner*—Anhtuan T. Nguyen
*Assistant Examiner*—Michael M Thompson
(74) *Attorney, Agent, or Firm*—Arlyn Alonzo; Lyon & Lyon (57) ABSTRACT

A catheter using multiple hollow fibers to carry a heating/cooling fluid employs fiber spreading features to improve heat transfer and help prevent clotting of body fluids within which the catheter is immersed. The catheter includes a length of outer tube surrounding an inner tube. The inner tube conveys fluids in one direction, and the passageway between inner and outer tubes conveys fluids in the opposite direction. The inner and outer tubes have proximal distal ends. The distal end is closed, but the proximal end is open to permit introduction of a heating or cooling fluid into the inner tube, and withdrawal of the fluid from the passageway between the inner and outer tubes. At the tubes' distal end resides a proximal fluid transfer housing coupled to multiple hollow heat exchange fibers. The distal ends of these fibers may be commonly connected to a distal fluid transfer housing and optional reservoir, which cooperatively return fluid to the passageway between inner and outer tubes. In another embodiment, each fiber includes both outflowing and return lumens, enabling the fibers' distal ends to freely move about. In another embodiment, each fiber proceeds outward from the proximal fluid transfer housing, and returns back to form a loop. In each different embodiment, the invention includes one or more actuating structures to spread the fibers. The actuating structure may include, for example, fiber shaping, a retractable spreading member, elastic bias built into the fibers, etc.

14 Claims, 6 Drawing Sheets

U.S. PATENT DOCUMENTS

| | | |
|---|---|---|
| 3,776,241 A | 12/1973 | Magilton et al. |
| 3,897,790 A | 8/1975 | Magilton et al. |
| 3,913,581 A | 10/1975 | Ritson |
| 4,010,795 A | 3/1977 | Stenberg |
| 4,111,209 A | 9/1978 | Wolvek et al. |
| 4,154,245 A | 5/1979 | Daily |
| 4,249,923 A | 2/1981 | Walda |
| 4,298,006 A | 11/1981 | Parks |
| 4,416,280 A | 11/1983 | Carpenter et al. |
| 4,416,281 A | 11/1983 | Cooper et al. |
| 4,583,969 A | 4/1986 | Mortensen |
| 4,672,962 A | 6/1987 | Hershenson |
| 4,745,922 A | 5/1988 | Taylor |
| 4,748,979 A | 6/1988 | Hershenson |
| 4,750,493 A | 6/1988 | Brader |
| 4,754,752 A | 7/1988 | Ginsberg et al. |
| 4,759,349 A | 7/1988 | Betz et al. |
| 4,791,930 A | 12/1988 | Suzuki et al. |
| 4,813,210 A | 3/1989 | Masuda et al. |
| 4,823,076 A | 4/1989 | Haines et al. |
| RE32,983 E | 7/1989 | Levy |
| 4,844,074 A | 7/1989 | Kurucz |
| 4,850,958 A * | 7/1989 | Berry et al. ............... 604/26 |
| 4,860,744 A | 8/1989 | Johnson et al. |
| 4,883,455 A | 11/1989 | Leonard |
| 4,899,741 A | 2/1990 | Bentley et al. |
| 4,920,963 A | 5/1990 | Brader |
| 4,941,475 A | 7/1990 | Williams et al. |
| 4,987,896 A | 1/1991 | Nakamatsu |
| RE33,561 E | 3/1991 | Levy |
| 5,019,075 A | 5/1991 | Spears et al. |
| 5,021,045 A | 6/1991 | Buckberg et al. |
| 5,037,383 A * | 8/1991 | Vaslef et al. ............... 604/26 |
| 5,041,089 A | 8/1991 | Mueller et al. |
| 5,066,578 A | 11/1991 | Wikman-Coffelt |
| 5,078,713 A | 1/1992 | Varney |
| 5,092,841 A | 3/1992 | Spears |
| 5,098,376 A | 3/1992 | Berry et al. |
| 5,106,360 A | 4/1992 | Ishikawa et al. |
| 5,139,496 A | 8/1992 | Hed |
| 5,147,355 A | 9/1992 | Friedman et al. |
| 5,147,385 A | 9/1992 | Beck et al |
| 5,151,100 A | 9/1992 | Abele et al. |
| 5,158,534 A | 10/1992 | Berry et al. |
| 5,174,285 A | 12/1992 | Fontenot |
| 5,182,317 A | 1/1993 | Winters et al. |
| 5,191,883 A | 3/1993 | Lennox et al. |
| 5,196,024 A | 3/1993 | Barath |
| 5,211,631 A | 5/1993 | Sheaff |
| 5,230,862 A | 7/1993 | Berry et al. |
| 5,248,312 A | 9/1993 | Langberg |
| 5,250,070 A | 10/1993 | Parodi |
| 5,257,977 A | 11/1993 | Eshel |
| 5,261,399 A | 11/1993 | Klatz et al. |
| 5,262,451 A | 11/1993 | Winters et al. |
| 5,269,758 A | 12/1993 | Taheri |
| 5,275,595 A | 1/1994 | Dobak, III |
| 5,279,598 A | 1/1994 | Sheaff |
| 5,281,213 A | 1/1994 | Milder et al. |
| 5,281,215 A | 1/1994 | Milder |
| 5,324,286 A | 6/1994 | Fowle |
| 5,338,770 A | 8/1994 | Winters et al. |
| 5,342,301 A | 8/1994 | Saab |
| 5,342,693 A | 8/1994 | Winters et al. |
| 5,354,277 A | 10/1994 | Guzman et al. |
| 5,411,477 A | 5/1995 | Saab |
| 5,423,807 A | 6/1995 | Milder |
| 5,437,673 A | 8/1995 | Baust et al. |
| 5,452,582 A | 9/1995 | Longsworth |
| 5,478,309 A | 12/1995 | Sweezer et al. |
| 5,486,204 A | 1/1996 | Clifton |
| 5,486,208 A | 1/1996 | Ginsberg |
| 5,531,776 A | 7/1996 | Ward et al. |
| 5,545,161 A | 8/1996 | Imran |
| 5,562,606 A | 10/1996 | Huybregts |
| 5,609,620 A | 3/1997 | Daily |
| 5,624,392 A | 4/1997 | Saab |
| 5,655,548 A | 8/1997 | Nelson et al. |
| 5,656,420 A | 8/1997 | Chien |
| 5,693,080 A | 12/1997 | Wallstén et al. |
| 5,702,435 A | 12/1997 | Maytal |
| 5,716,386 A | 2/1998 | Ward et al. |
| 5,733,319 A | 3/1998 | Neilson et al. |
| 5,735,809 A | 4/1998 | Gorsuch |
| 5,758,505 A | 6/1998 | Dobak, III et al. |
| 5,759,182 A | 6/1998 | Varney et al. |
| 5,787,715 A | 8/1998 | Dobak, III et al. |
| 5,837,003 A | 11/1998 | Ginsberg |
| 6,126,684 A * | 10/2000 | Gobin et al. ............... 604/113 |

* cited by examiner

CATHETER WITH MULTIPLE HEATING/COOLING FIBERS EMPLOYING FIBER SPREADING FEATURES

CROSS-REFERENCE TO RELATED APPLICATIONS

This application is a continuation-in-part of U.S. application Ser. No. 09/133,813, entitled "Indwelling Heat Exchange Catheter and Method of Using Same," filed on Aug. 13, 1998. The foregoing application will be referred to as the parent '813 application.

BACKGROUND OF THE INVENTION

1. Field of the Invention

The present invention relates to catheters that effect heat exchange using a bundle of multiple hollow fibers.

2. Description of the Related Art

In warm blooded creatures, temperature regulation is one of the most important functions of the body. Despite the known importance of properly maintaining body temperature, scientists have discovered certain beneficial effects of artificially inducing a hypothermic state. For instance, cooling the body can help regulate vital functions during surgery by lowering the metabolism. With stroke, trauma, and other pathological conditions, hypothermia also reduces the permeability of the blood/brain barrier. Also, induced hypothermia inhibits the release of damaging neurotransmitters, inhibits calcium mediated effects, inhibits brain edema, and lowers intra cranial pressure. Regardless of the particular mechanism, the present invention understands that fevers degrade the outcomes for patients suffering from brain trauma or ischemic, and moreover that hypothermia improves the outcomes for such patients.

Hypothermia may be induced locally or systemically. With local hypothermia, physicians focus their cooling efforts on a particular organ, limb, anatomical system, or other region of the body. With systemic hypothermia, doctors universally lower body temperature without particular attention to any body part.

Under one technique for inducing systemic hypothermia, physicians cool the patient's entire body by packing it in ice. Although this technique has been used with some success, some physicians may find it cumbersome, and particularly time consuming. Also, it is difficult to precisely control body temperature with ice packing. As a result, the patient's body temperature overshoots and undershoots the optimal temperature, requiring physicians to add or remove ice. Furthermore, there is some danger of injuring the skin, which is necessarily cooled more than any other body part.

In another approach to systemic hypothermia, the patient is covered with a cooling blanket, such as an inflatable air- or water-filled cushion. Beneficially, cooling blankets offer improved temperature control because physicians can precisely regulate the temperature of the inflation medium. Nonetheless, some delay is still inherent, first for a cooling element to change the temperature of the cooling medium, and then for the temperature adjusted cooling medium to cool the desired body part. This delay is even longer if the targeted body part is an internal organ, since the most effective cooling is only applied to the skin, and takes some time to successively cool deeper and deeper layers within the body.

The present invention recognizes that a better approach to inducing hypothermia is by circulating a cooling fluid through a cooling catheter placed inside a patient's body. The catheter may be inserted into veins, arteries, cavities, or other internal regions of the body. The present assignee has pioneered a number of different cooling catheters and techniques in this area. Several different examples are shown in the parent '813 application, which is hereby incorporated into the present application by reference.

Advantageously, cooling catheters are convenient to use, and enable doctors to accurately control the temperature of a targeted region. In this respect, cooling catheters constitute a significant advance. Nonetheless, the performance, efficiency, safety, and reliability of these catheters can be improved. One area of possible improvement concerns the prevention of blood clots, which can arise any time a foreign object is inserted into the bloodstream.

SUMMARY OF THE INVENTION

Broadly, the present invention concerns a catheter with multiple hollow fibers that carry a coolant fluid, where one or more fiber spreading features are employed to improve heat exchange with body fluids surrounding the catheter, as well as other benefits. Catheters constructed according to this invention generally include a length of outer tube surrounding an inner tube. The inner tube conveys fluids in one direction, whereas the passageway between the inner and outer tube conveys fluids in the opposite direction. The inner and outer tubes have proximal and distal ends. The tubes' proximal ends are open to permit introduction (or withdrawal) of a heating or cooling fluid into the inner tube and withdrawal (introduction) of the fluid from the passageway between the inner and outer tubes. At the distal end of the tubes, a proximal fluid transfer housing is attached to multiple hollow heat exchange fibers.

One embodiment is called "bound tip," because the fibers are bound together at the catheter's distal tip. In this embodiment; the fibers continue from the proximal fluid transfer housing to a distal fluid transfer housing, attached to a reservoir. The proximal fluid transfer housing forms a sealed fluid path between the fibers and the passageway. The distal fluid transfer housing forms a sealed fluid path between the opposite ends of the fibers and the fluid reservoir and the inner tube. Fluid starts a continuous path by flowing from the inner tube's proximal end toward its distal end. The proximal fluid transfer housing redirects fluid into the hollow fibers, where the fluid flows until it reaches the distal fluid transfer housing. The distal fluid transfer housing directs fluid into the reservoir, and then into the return passageway between the inner and outer tubes to complete the path. It is to be understood that, in a different embodiment, fluid could flow in the opposite direction as well.

A different embodiment is called "free tip" because the fibers are not bound at the catheter's tip. This embodiment eliminates the distal fluid transfer housing and reservoir. Here, each hollow fiber incorporates an outflowing lumen and a return lumen. In this embodiment, the proximal fluid transfer housing not only directs fluid into the outflowing lumens, but also guides fluid from the return lumens into the passageway between the inner and outer tubes.

In a different "free tip" embodiment, the distal fluid transfer housing and reservoir are also omitted. However, each hollow fiber extends outward from the proximal fluid transfer housing and returns back again, forming a loop. Thus, the proximal fluid transfer housing not only directs fluid into one end of each hollow fiber, but also guides fluid from the opposite end of each fiber into the passageway between the inner and outer tubes.

In each of the foregoing embodiments, the invention includes actuating structure to spread the fibers under certain conditions. The actuating structure may include, for example, an elastic bowing built into the fibers to automatically curve them outward from the inner tube when there is insufficient fiber straightening pressure on the fibers. Alternatively, the fibers may be formed with shape memory, causing them to adopt a predetermined shape in response to certain temperature conditions. In another example, some or all of the fibers are pre-shaped to form spirals of predetermined amplitude and phase. In still another embodiment, the actuating structure may be provided by a spreading member coupled to a retraction line that runs within the outer tube from its distal end to its proximal end; withdrawal of the retraction line pulls the spreading member toward the common proximal ends of the fibers thereby moving the fibers apart.

The invention may be implemented in various forms, such as an apparatus or a method. An example of the apparatus is a multifiber heat exchange catheter, with various fiber spreading features. Examples of the method aspect of this invention include techniques for using or manufacturing a multifiber heat exchange catheter, etc.

The invention affords its users with a number of distinct advantages. Chiefly, by spreading the heating/cooling fibers the invention helps prevent clotting of blood or other body fluids that surround the catheter. In addition, with more widely distributed fibers, the catheter of this invention can cool the nearby tissue more efficiently. The invention also provides a number of other advantages and benefits, which should be apparent from the following description of the invention.

DETAILED DESCRIPTION

The nature, objectives, and advantages of the invention will become more apparent to those skilled in the art after considering the following detailed description in connection with the accompanying drawings. As mentioned above, the invention concerns a multifiber heat exchange catheter that includes various fiber spreading features such as a squid shaped end.

HARDWARE COMPONENTS & INTERCONNECTIONS

Catheter Types

Introduction

Chiefly, the invention concerns a multifiber heat exchange catheter, which may be embodied by various hardware components and interconnections. The invention includes various embodiments with features designed to spread the fibers while the catheter is being used. Important features of this catheter are found at the tip of the catheter, which is either "free" or "bound." In either case, coolant fluid travels longitudinally out and back through a sealed path inside the catheter, without contacting the tissue or body fluid surrounding the catheter. Broadly, "free tip" catheters direct a coolant into multiple hollow fibers with free floating ends. The coolant runs out and back within each fiber individually. Accordingly, the fibers include individual redirecting structure to direct the coolant back down each fiber. With "bound tip" catheters, coolant travels in one direction through a first conduit, and returns in an opposite direction through hollow fibers and then a second conduit. In this embodiment, the redirecting structure is provided by a fluid transfer housing. The fluid transfer housing, coupled to the fibers and an optional fluid collection reservoir, redirects fluid between outbound and inbound paths.

The coolant comprises a fluid having suitable properties of heat transfer, biocompatibility, viscosity, etc. The coolant may be a liquid or gas, with saline being one example.

Bound Tip Catheter

Figure 1:
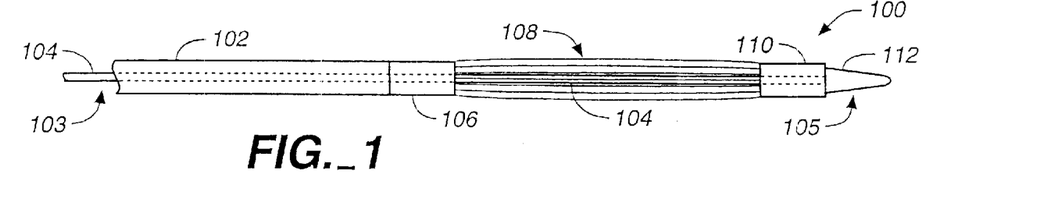
FIG. 1 is a plan view of a "bound tip" multifiber heat exchange catheter, in accordance with the invention.

FIG. 1 shows a catheter 100 that exemplifies the bound tip type. The catheter 100 includes an outer tube 102 containing an inner tube 104. The outer tube 102 comprises a suitably flexible and nonallergenic material with consistent mechanical performance over a range of expected temperatures such as 0–40° Celsius. Some exemplary materials include polyether amide block copolymers, urethane materials, and the like. In embodiments using a circular cross section, the outer tube 102 may have a diameter of about 1–5 millimeters, with 4 millimeters as a specific example. The inner tube 104 may be formed from similar material as the outer tube 102, with a diameter in the range of 0.075 inches. If desired to conserve space, the inner tube 104 may have a higher durometer (hardness) rating than the outer tube 102, with correspondingly thinner walls.

Although not required, the tubes 102/104 may be concentric. The inner tube 104 provides one fluid path, and the passageway between the inner and outer tubes 104/102 provides a second, opposite direction fluid path. The tubes 102/104 progress from the catheter's proximal end 103 toward its distal end 105. In use, the proximal ends of the tubes 102/104 may be coupled (not shown) to a coolant source, such as one or more syringes, mechanized pumps, hand pumps, gravity feed systems, or another appropriate device for circulating a coolant fluid through the catheter 100.

The specific arrangement of outer tube and concentric inner tube shown FIG. 1 and throughout the application is merely one exemplary embodiment. The invention also contemplates other arrangements providing two conduits coupled via the fibers to form a continuous fluid conveyance path. As a different example, the conduits may be bonded side-by-side, or may be completely separate tubes. These tubes may be enclosed by a third tube, molded together, or otherwise manufactured to form a smooth continuous outer surface, if desired.

At the distal end of the outer tube 102, the tube 102 couples to a proximal fluid transfer housing 106, the construction and purpose of which are discussed below. The inner tube 104 continues through the proximal fluid transfer housing, ending at a distal fluid transfer housing 110. Between the fluid transfer housings 106/110 lie multiple hollowfibers 108. At the catheter's distal end 105 a fluid collecting reservoir 112 is coupled to the distal fluid transfer housing 110. Alternatively, the depicted fluid collecting reservoir 112 may be omitted, with the reservoir function being established by the distal fluid transfer housing itself. Each fluid transfer housing defines a fluid passageway, this void being referred to as a "plenum" (not shown).

The fibers 108 are made from a suitably flexible, nonallergenic, material such as polyurethane or polyethylene, or another material that is safe for internal use in the body and has suitable heat exchange properties. Although the number of fibers 108 may vary among applications, and the size of fibers 108 may even vary in a single catheter construction, an exemplary embodiment uses about 22–24 fibers having an outer diameter of 0.022 inches and an inner diameter of about 0.0185 inches.

The bases of the fibers, where they attach to the fluid transfer housings 106/110, may be arranged in any desired configuration. At each fluid transfer housing, for example, the fibers' bases may form concentric rings, a random pattern, a grid, a spiral, a longitudinal taper, etc.

In use, coolant is injected or pumped from the proximal end 103 into the inner tube 104. The distal fluid transfer housing 110 directs the fluid exiting the inner tube 104 into the fluid collecting reservoir 112. Due to positive pressure upon fluid arriving from the inner tube 104, the fluid exits the reservoir 112 and passes through tiny holes in the distal fluid transfer housing 110 into the individual fibers 108. While traversing the fibers, the fluid removes body heat because of the fibers' thin walls and their substantial surface area that is exposed to the surrounding liquid (e.g., arterial or venous blood, etc.) that immerses the catheter 100.

An anticlotting agent, such as heparin, may be applied to the fibers 108 and other parts of the catheter 100 that are exposed to the patient's blood. Although not mentioned specifically elsewhere, anticlotting materials may also be applied to some or all of the exterior components of the other catheters discussed below.

Free Tip Catheter

In contrast to the embodiment of FIG. 1, FIG. 2 and 2A–2C illustrate an example 200 of the free tip catheter in greater detail. The catheter 200 includes an outer tube 202 containing an inner tube 204. The tubes 202/204 may have similar construction and configuration as the tubes in previously described catheter 100. The tubes 202/204 progress from the catheter's proximal end 203 toward its distal end 205. In use, the proximal ends of the tubes 202/204 may be coupled (not shown) to a coolant source, as discussed above in the context of the catheter 100.

Figure 2:
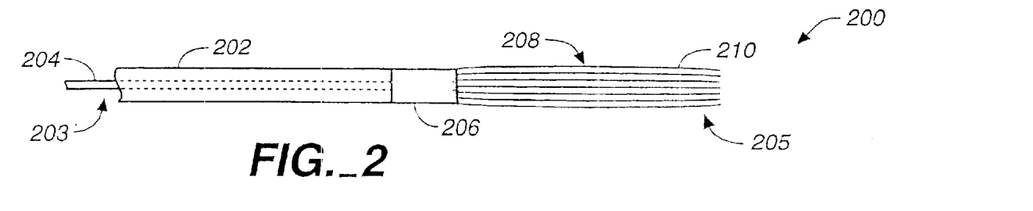
FIG. 2 is a plan view of one "free tip" multifiber heat exchange catheter, in accordance with the invention.
Figure 2A:
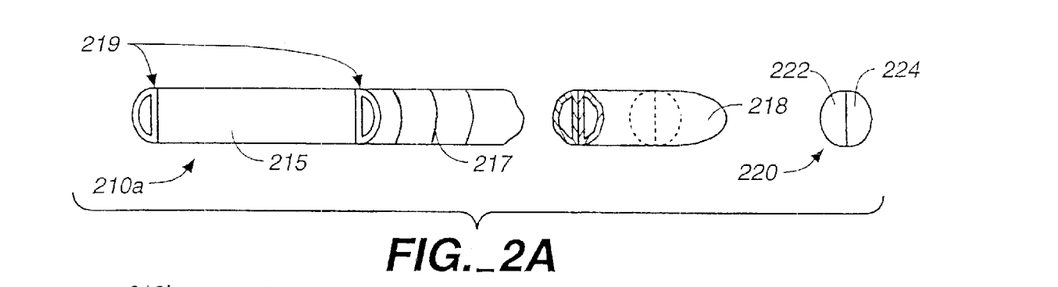
FIG. 2A is a cutaway perspective view of one dual lumen fiber from the catheter of FIG. 2, in accordance with the invention.

At the distal end of the tubes 202/204, the tubes couple to a fluid transfer housing 206, the construction and purpose of which are discussed below. The fluid transfer housing 206 is coupled to multiple hollow heat exchange fibers 208, such as the fiber 210. Each fiber, such as 210, includes two channels that each define a fluid passageway or "lumen." The channels may have "D" shaped cross sections 220 (FIG. 2A) or concentric circular cross sections 256 (FIG. 2B), for example. In the example of FIG. 2A, the representative fiber 210a defines a first channel 215 and a second channel 217; the fluid passage in each channel is referred to as a "lumen." The channels are adjoined along the flat portion of their "D" shaped cross sections to form a common wall. Coolant can pass from one lumen to the other at a tip reservoir 218 that comprises a cap covering the channels' ends. Namely, the tip reservoir 218 receives fluid from the fluid transfer housing 206 via one of the lumens, and redirects this outbound fluid down the other lumen back toward the fluid transfer housing. The fiber tips can also be radiopaque or the fibers themselves can be radiopaque or visualized by filling with contrast media. The proximal ends 219 of the channels 215/217 are staggered to help interface the channels with the fluid transfer housing 206, as discussed below.

Figure 2B:
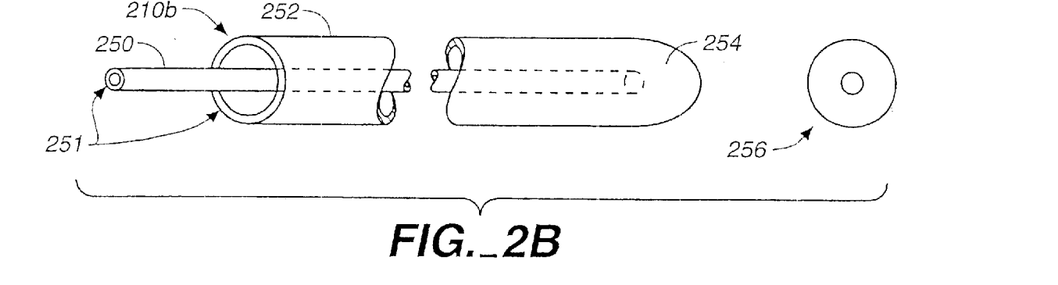
FIG. 2B is a cutaway perspective view of another type of dual lumen fiber from the catheter of FIG. 2, in accordance with the invention.

In the example of FIG. 2B, the representative fiber 210b includes an inner channel 250 and an outer channel 252 that exchange fluid in a tip reservoir 254. The tip reservoir 254 receives fluid from the fluid transfer housing 206 via one of the channels, and redirects this outbound fluid back down the other channel toward the fluid transfer housing 206. The proximal ends 251 of the lumens 250/252 are longitudinally staggered to help interface the channels with the fluid transfer housing 206, as discussed below.

Figure 2C:
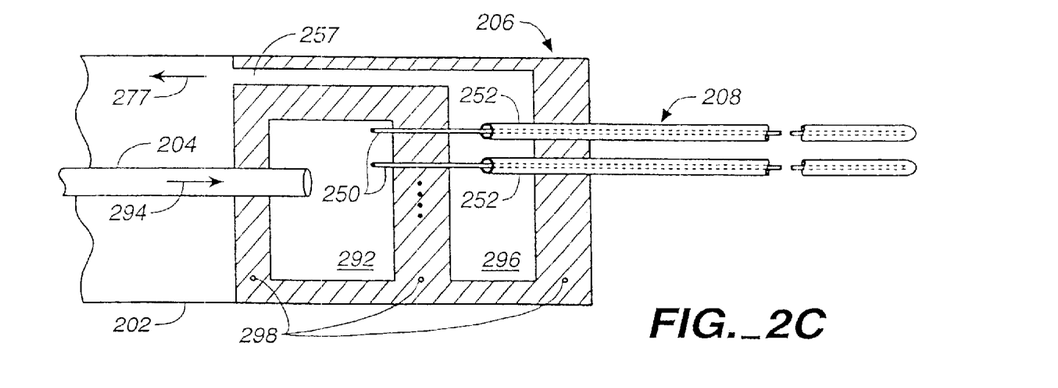
FIG. 2C is a detailed cross-sectional diagram showing the construction of a fluid transfer housing from the catheter of FIG. 2, in accordance with the invention.

FIG. 2C shows the fluid transfer housing 206 in greater detail. The fluid transfer housing 206 is described in the context of the channels 250/252 (FIG. 2B), although this discussion is similarly applicable to fibers of the type shown in FIG. 2A. The fluid transfer housing 206 includes two internal reservoirs 292, 296. In this example, the first reservoir 292 provides a site for fluid to exchange between the inner tube 204 and the inner channels 250. The second reservoir 296 provides a site to exchange fluid between (1) the passageway between the outer tube 202 and the inner tube 204 and (2) the passageways between each inner channel 250 and its respective outer channel 252. The reservoir 296 has an opening 257 connecting the reservoir 296 to the passageway between the inner tube 204 and the outer tube 202.

Referring to FIGS. 2, 2B, and 2C, the catheter is operated by injecting or pumping coolant into the inner tube 204 at the catheter's proximal end 203. The fluid flows through the inner tube 204 in the direction 294. The inner tube 204 directs this fluid into the reservoir 292, where positive pressure on the fluid continues fluid flow into the inner channels 250. Fluid in each channel 250 passes distally to its tip reservoir 254, then returns through the passageway between inner and outer channels 250/252. While traversing fibers, the coolant removes heat from the body fluid surrounding the catheter (e.g., blood). Fluid returning through the fibers 208 travels through the passageways between inner and outer channels 250/252 and then into the reservoir 296. Due to the opening 257, the fluid transfer housing 206 directs fluid from the reservoir 296 into the passageway between the inner and outer tubes 204/202. Of course, the reverse fluid path may be used instead, without departing from the scope of this invention.

One advantage of the construction of the catheter 200 is that the catheter's fibers are free floating at their distal ends. In this respect, the fiber bundle has a squid-like shape. Namely, the fibers 208 are not bound at their distal ends. This permits the fibers to move about and effect greater heat transfer, and also reduces the possibility of forming blood clots because (1) there are fewer constricting joints to impede blood flow, and (2) the free moving fibers are less likely to lay against the wall of a vein or artery or against each other.

Figure 3:
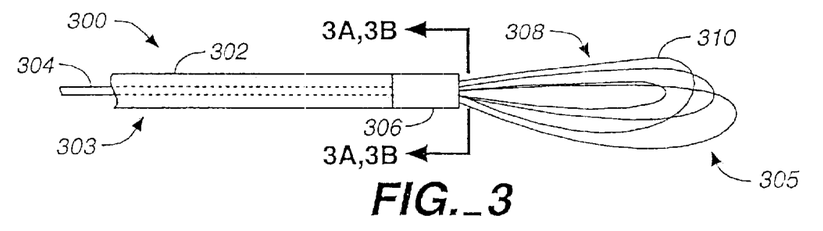
FIG. 3 is a plan view of another free tip catheter, where each fiber projects out and returns to the fluid transfer housing to form a loop, in accordance with the invention.

FIG. 3 illustrates a different embodiment 300 of a free tip catheter. The catheter 300 includes an outer tube 302 containing an inner tube 304. The tubes 302/304 may have similar construction and configuration as the tubes of previously described catheter 100. The tubes 302/304 progress from the catheter's proximal end 303 toward its distal end 305. In use, the proximal ends of the tubes 302/304 may be coupled (not shown) to a coolant source, as discussed above in the context of the catheter 100.

The tubes 302/304 end at a fluid transfer housing 306. The fluid transfer housing 306 is coupled to multiple hollow heat exchange fibers 308, such as the fiber 310. Each fiber has two ends, and both ends are coupled to the fluid transfer housing 306. In a preferred embodiment, seven fibers 308 are used, each having the dimensions described above for the fibers 108. Each fiber forms a loop. To ameliorate the effects of kinking, the distal loop of each fiber is heat formed in a tight U-shaped bight. For applications where the catheter 300 is to be immersed in blood, the fibers preferably comprise a material that is less dense than blood, such as polyolefin.

The fluid transfer housing 306 directs fluid from the inner tube 304 into a coolant supply end of each fiber 308. The fluid transfer housing 306 also receives return fluid from a coolant return end of each fiber 308, and directs this return fluid into the passageway between the inner tube 304 and outer tube 302. The invention also contemplates a fluid path in the exact opposite direction.

As with the catheter 200, one advantage of the catheter 300 is the catheter's free distal tip; the distal tip or end is "free" in that the fibers 308 are not bound at the distal-most location. In addition to permitting the fibers to move about and effect greater heat transfer, this also reduces the possibility of forming blood clots because (1) there are fewer constricting joints to impede blood flow and (2) the free moving fibers are less likely to lay against the wall of a vein or artery or against each other.

In use, a coolant is fed into the inner tube 304 at the catheter's proximal end 303. The fluid transfer housing 306 directs the fluid into the coolant supply end of each of the fibers 308. The coolant passes through each fiber, from the fiber's coolant supply end to its coolant return end. The fluid transfer housing 306 receives fluid returning through the fibers' coolant return ends, and directs this fluid into the passageway between the inner and outer tubes 304/302. While traversing the fibers, the fluid experiences significant heat exchange for the same reasons discussed above.

Figure 3A:
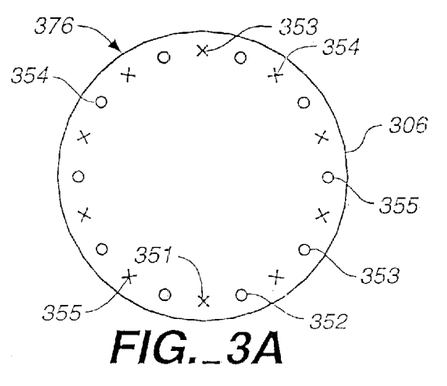
FIG. 3A is an end view of one embodiment of the catheter of FIG. 3, in accordance with the invention.

The looped fibers 308 of the catheter 300 may be arranged in many different ways in terms of where they are coupled to the fluid transfer housing 306. One example appears in FIG. 3A, which shows an end view of the fibers 308 distally of the fluid transfer housing 306. FIG. 3A depicts each coolant return end as an "X" (e.g., 351), and each coolant supply end as an "O" (e.g., 352). In FIG. 3A, the opposite ends of three individual fibers are identified by 353, 354, and 355. In this embodiment, the fibers are arranged so that each fiber exits the fluid transfer housing 306, loops around, and reenters the fluid transfer housing several positions away from its exit point. The fibers exit/entry points form a ring 376 around the perimeter of the fluid transfer housing 306.

Figure 3B:
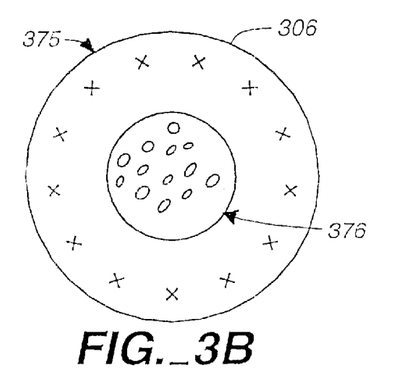
FIG. 3B is an end view of the free tip catheter of FIG. 3A, modified to include multiple fibers rings, in accordance with the invention

Many different variations of fiber layout are possible. For instance, rather than the fluid transfer housing exit/entry points shown in FIG. 3A, each fiber may exit/enter the fluid transfer housing 306 so as to span the full width (not shown) of the fluid transfer housing 306, to form adjacent entry/exit points, or to form another arrangement. Fibers may exit and enter randomly (not shown) from various points across the fluid transfer housing 306. FIG. 3B shows a different embodiment, with an outer ring 375 of coolant return ends and an inner ring 376 of coolant supply ends. The two ends of each fiber are mounted to the housing 306 as follows: one end in the ring 375 and the other end in the ring 376.

Actuating Structure

Whether bound tip or free tip, catheters of this invention can additionally include one or more actuating structures that serve to spread the heat exchange fibers under certain circumstances. Spreading the fibers boosts the efficacy of the heat exchange process. Additionally, fiber spreading helps prevent the formation of clots in the blood or other liquid that immerses the catheter. Free tip catheters help avoid clots because they minimize the number of constricting joints that necessarily impede blood flow. Free and bound tip catheters, as discussed below, may include certain features that permit heat exchange fibers to move more freely, and thereby minimize the clots caused by fibers laying against the wall of a vein or artery. As discussed below, actuating structure is either self actuated or externally actuated.

Self Actuated: Natural

Self actuated fiber spreading mechanisms operate automatically, without the need for physicians to manually actuate fiber spreading. One example is the fibers 208 of the free tip catheter 200, which naturally spread to some extent while inserted into the bloodstream, due to the flow of liquid (e.g., blood) between and around the fibers 208 and relatively low density of the fibers. The same is true for the fibers 308 of the catheter 300, which are free to move and spread out.

Self Actuated: Shaped

OUTWARD CURVES/BOWING

Figure 4:
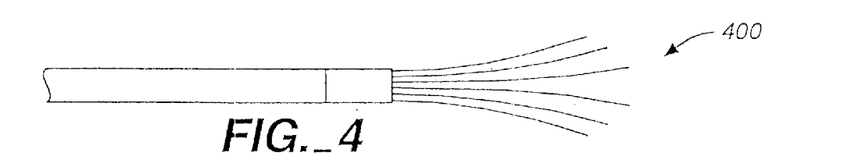
FIG. 4 is a plan view of a free tip catheter with pre-shaped fibers, in accordance with the invention.

Another self actuated fiber spreading mechanism is constructed by pre-forming the fibers into shapes that introduce a desired level of fiber spreading. FIG. 4 shows one example, in the context of the free tip catheter 200. Namely, the fibers 400 are "pre-shaped," meaning that the fibers have been manufactured such that each fiber tends to return to a designated shape, due to built-in elastic biasing. In other words, if a straightening force is applied to the fiber and then released, the pre-shaped fiber automatically tends to return to its pre-shaped form due to its heat shaping.

Another type of shaping is selectively triggered by temperature, rather than always biasing the fibers toward a particular shape. In this embodiment, the fiber may assume different shapes at different temperatures. This is called "shape memory," and may be implemented with shape memory polymers or other materials with similar properties.

Figure 5:
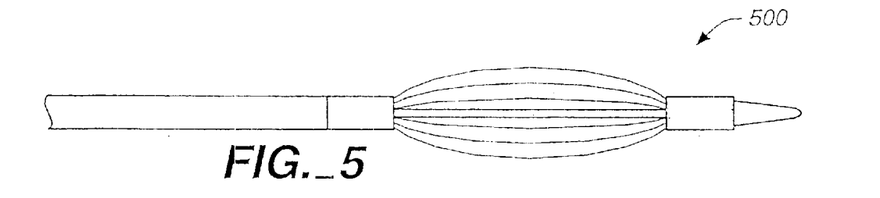
FIG. 5 is a plan view of a bound tip catheter with pre-shaped fibers, in accordance with the invention.

The shaping of fibers may be introduced by heat shaping, extruding, molding, or other suitable techniques, e.g., by choice of polymer. FIG. 5 shows another example of preformed fibers, in the context of the bound tip catheter 100. In this example, the fibers 500 are pre-shaped with some material bias, tending to bow the fibers 500 outward. As an alternative, the fibers may be conditioned with shape memory so that they are straight at room temperature (FIG. 1), but assume a bowed form (FIG. 5) at a predetermined temperature, such as internal body temperature (e.g., about 37° Celsius). The fibers are made from a suitably flexible, nonallergenic, material such as polyurethane or polyethylene, or another material that is safe for internal use in the body. As an example, each fiber may have an outer diameter of 0.022 inches, an inner diameter of about 0.0185 inches, and a length of about 20 centimeters, and 23 fibers are provided. Of course, the number and dimensions of the fibers may vary among applications, and fibers of varying dimensions may even present in a single catheter.

Shaped fibers may be made from a variety of suitably flexible, nonallergenic, material such as polyurethane or polyethylene, or another material that is safe for internal use in the body. Specific examples include shape memory polymers manufactured by Nippon Zeon, Kuraray, or Asahi, or shape memory polyurethane materials made by the Nagiya Research and Development Center of Mitsubishi Heavy Industry, or by Polymer Technology Group.

SPIRALS

Figure 6:
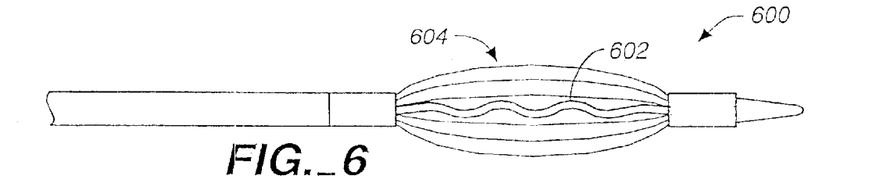
FIG. 6 is a plan view of a bound tip catheter with a spirally pre-shaped inner tube, in accordance with the invention.

FIG. 6 shows another self actuated fiber spreading mechanism that is useful in bound tip catheters. In this embodiment, the catheter 600 has an inner tube 602 with a spiral shape induced by pre-shaping or shape memory, which thereby urges the surrounding fibers 604 to spread out. The inner tube 602 may be spirally formed by heat treatment, extrusion, molding, or another pre-shaping technique.

One advantage of the spirally shaped inner tube 602 is its novel operational mode. In particular, by applying heat exchange fluid with pulsed pressure, the catheter adopts a corresponding movement. Namely, the inner tube 602 elongates in response to increased pressure (tending to straighten its spiral windings), and shortens responsive to decreased pressure. The movement of the inner tube 602 in turns creates movement in the surrounding fibers. Pulsed pressure may be applied to the catheter rhythmically, randomly, periodically, or according to another beneficial pattern or schedule. This movement improves heat transfer by disrupting the boundary layer of fluid surrounding the catheter, and also by flushing low or stagnant areas of fluid surrounding the fibers 602. As an additional benefit, this flushing action reduces the potential for creating clots in blood or other fluid surrounding the catheter because there is less potential for the moving fibers 604 to have prolonged contact with the surrounding vessel wall.

Instead of the spiral inner tube 602, or in addition thereto, the fibers 604 may be bowed, spirally shaped, or equipped with another form of pre-shaping or shape memory. Although not shown, the fibers in a free tip catheter may also be spirally shaped to enjoy similar benefits.

Figure 7:
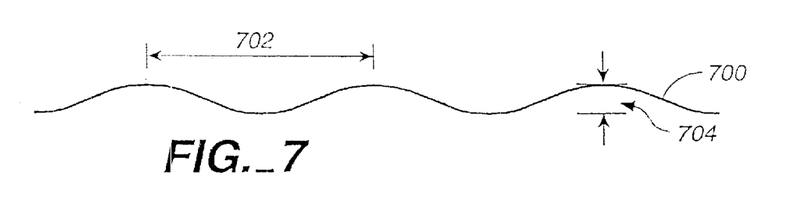
FIG. 7 is a diagram illustrating the measurement of period and amplitude for pre-shaped fibers and tubes, in accordance with the invention.

FIG. 7 diagrams a cross section of a spiral pattern that may be applied to fibers of a free or bound tip catheter, or to the inner tube of a bound tip catheter. The pattern 700 in this example is defined by a repeating shape having a period 702 defining the space between adjacent windings, and an amplitude 704 defining the magnitude of each winding.

Figure 8A:
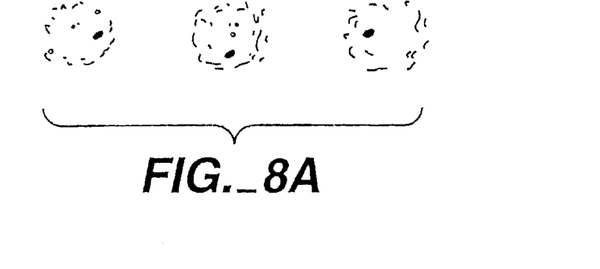
FIG. 8A is a sequential end view of a fiber bundle with synchronized spiraling, in accordance with the invention.
Figure 8B:
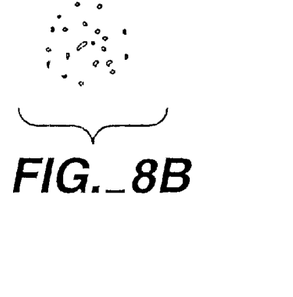
FIG. 8B is an end view of a fiber bundle with non-synchronized spiraling, in accordance with the invention.

The amplitude and pitch of fiber and/or inner tube spiral winding may be varied in different ways. In one embodiment, all fibers exhibit the same pitch and amplitude. Furthermore, some, all, or none of the fibers may be synchronized with each other to reach their amplitude peaks and troughs at the same position between the proximal and distal fluid transfer housings; as an example, FIG. 8B shows a fiber bundle cross section where there is considerable variance in spiral pitch and amplitude among the fibers. Furthermore, depending upon the application, there may be varying or single common right-hand turning or left-hand turning direction among the individual fibers and the inner tube. Different embodiments are also possible to vary one or more of the following characteristics among fibers, or between the fibers and the inner tube: pitch, amplitude, left/right hand spiral, or synchronization. For example, fibers on the periphery of the fiber bundle may exhibit one pitch, amplitude, and synchronicity, with interior fibers exhibiting a smaller (or larger) amplitude with the same pitch. FIG. 8A shows successive cross sectional views of the fiber bundle proceeding from the proximal fluid transfer housing to the distal fluid transfer housing (shown left to right), where all fibers exhibit the same pitch, amplitude, and left/right handedness, thereby moving identically as if they formed a single spiraling core about the inner tube. In addition, ordinarily skilled artisans, having the benefit of this disclosure, will recognize that a nearly endless number of further permutations are possible without departing from the scope of this invention.

Externally Actuated: Retractor

SINGLE STAGE

Figure 9:
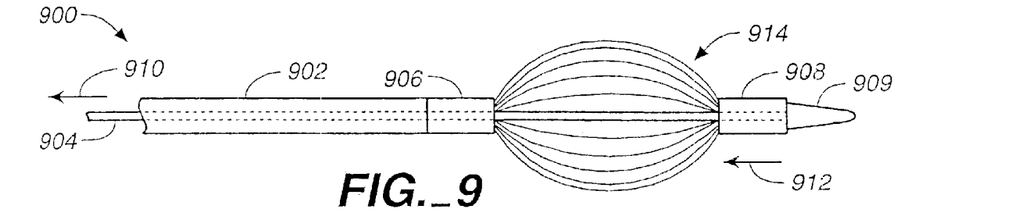
FIG. 9 is a plan view of a bound tip catheter with a slidably retractable inner tube for spreading heat exchange fibers, in accordance with the invention.

In contrast to the self actuated fiber actuating structures discussed above, the invention also contemplates catheters with various actuating structures that are externally or "manually" actuated. FIG. 9 shows a bound tip catheter 900 that exemplifies one specific type of manually operated retraction scheme. Many components of the catheter 900 are similar to those discussed above, and are therefore omitted from the present discussion for ease of illustration. Although the inner tube 904 resides within the outer tube 902 as discussed above, the inner tube 904 is slidably housed by the fluid transfer housing 906, forming a seal to prevent fluid leakage from passageway formed between the tubes 902/904 and the catheter's exterior. The inner tube 904 is secured to the fluid transfer housing 908. Thus, when a pulling force 910 is applied to the inner tube 904, withdrawal of the tube 904 pulls the fluid transfer housing 908 in the direction 912. This further causes the fixed length fibers 914 to bow as the distance between their ends shortens.

As with other fiber spreading mechanisms, this construction encourages the fibers to move about and effect greater heat transfer. In addition, this fiber spreading also reduces the possibility of forming blood clots because the loose fibers minimize blood flow disturbance, and are less likely to lay against the wall of a vein or artery or against each other.

MULTI STAGE

Figure 10:
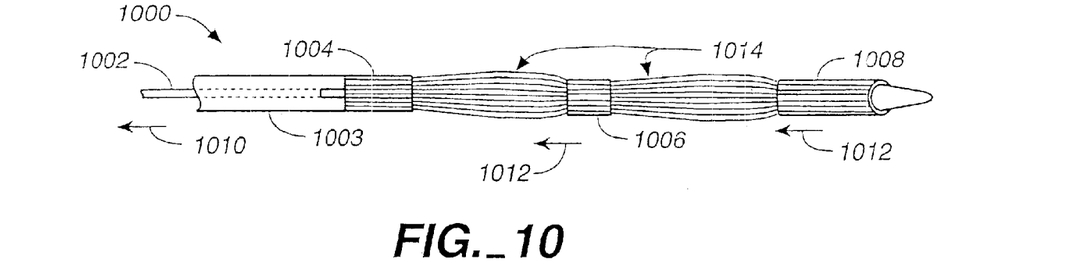
FIG. 10 is a perspective view of a bound tip catheter with a multi stage slidably retractable inner tube for spreading heat exchange fibers, shown in its unretracted state, in accordance with the invention.

FIG. 10 shows a bound tip catheter 1000 that exemplifies another type of manually operated retraction scheme, similar to the single stage sliding retraction scheme of FIG. 9. Many components of the catheter 1000 are similar to those discussed above, and are therefore omitted from the present discussion for ease of illustration. The inner tube 1002 resides within the outer tube 1003, and is slidably housed by a proximal fluid transfer housing 1004, but fixedly attached to a distal fluid transfer housing 1008. The catheter 1000 also includes an intermediate band 1006, within which the inner tube 1002 is slidably housed. The fibers 1014 pass through and are attached to the intermediate band 1006. The band 1006 may be manufactured from polyolefin, polyurethane, nylon, or another material with suitable qualities of strength and biocompatibility.

Figure 11:
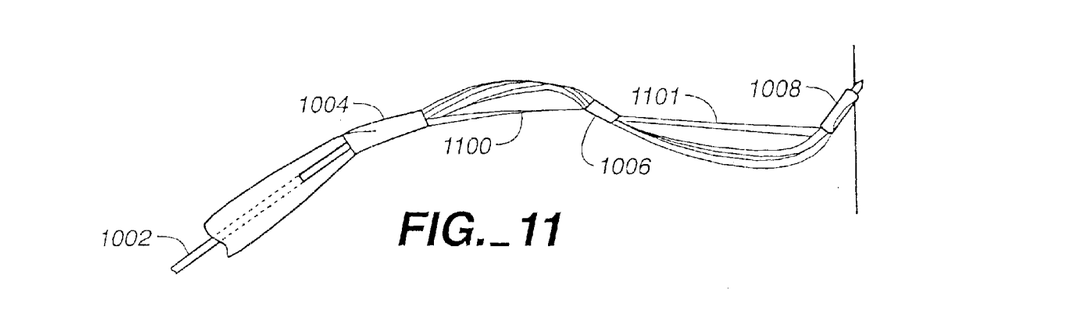
FIG. 11 is a perspective view of the bound tip catheter of FIG. 10, in its retracted state, in accordance with the invention.

When a pulling force 1010 is applied to the inner tube 1002, withdrawal of the tube 1002 slides the tube 1002 through the proximal fluid transfer housing 1004 but pulls the band 1006 and the fluid transfer housing 1008 in the direction 1012. This causes the fixed-length fibers 1014 to bow between the fluid transfer housing 1004 and the band 1006, and also to bow between the band 1006 and the fluid transfer housing 1008. In its retracted state, the catheter thus forms an "S" shape, as shown by FIG. 11.

BRAIDED SINGLE STAGE

Figure 12:
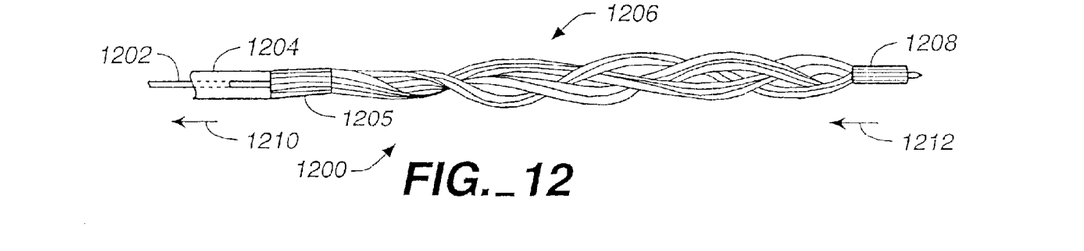
FIG. 12 is a perspective view of a bound tip catheter with interwoven heat exchange fibers and a slidably retractable inner tube for spreading these fibers, shown in its unretracted state, in accordance with the invention.

FIG. 12 shows another embodiment of bound tip catheter 1200, which utilizes single stage retraction as shown in FIG. 9. Many components of the catheter 1200 are similar to those discussed above, and are therefore omitted from the present discussion for ease of illustration. The catheter 1200 includes fibers 1206 that are divided into groups and interwoven. In this example, the fiber groups are interwoven by braiding them, by sequentially and passing one group over another in rotation. Different fiber grouping and weaving styles may be used without departing from the scope of this invention.

Figure 13:
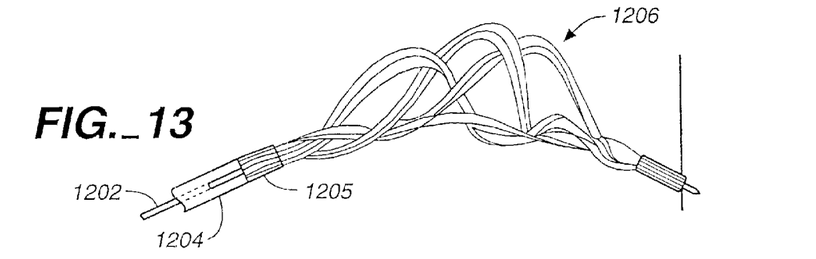
FIG. 13 is a perspective view of a bound tip catheter of FIG. 12, in its retracted state, in accordance with the invention.

The inner tube 1202 resides within the outer tube 1204 as shown in previously discussed embodiments. The inner tube 1202 is slidably housed by the proximal fluid transfer housing 1205 but secured to the distal fluid transfer housing 1208. The catheter 1200 includes fibers 1206 that are separated into three groups and braided. When a pulling force 1210 is applied to the inner tube 1202, withdrawal of the tube 1202 pulls the fluid transfer housing 1208 in the direction 1212. This causes the fixed-length fibers 1206 to bow while the distance between their ends closes, as shown in FIG. 13. The interweaving of the fibers helps to spread the fiber groups from each other even further.

SELECTIVELY INTERCONNECTED FIBERS

Figure 14:
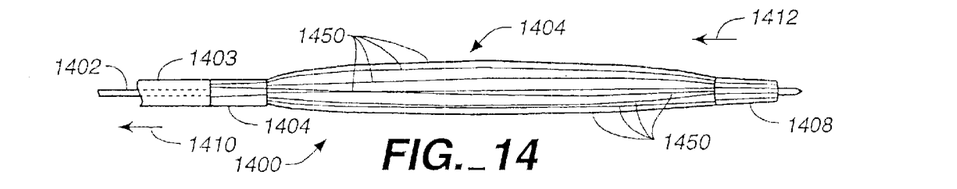
FIG. 14 is a plan view of a bound tip catheter with a slidably retractable inner tube for spreading heat exchange fibers, where the fibers are interconnected at various points, and the catheter is shown in its unretracted state, in accordance with the invention.

FIG. 14 shows a bound tip catheter 1400 that exemplifies a completely different type of manually operated retraction scheme. In this embodiment, the fibers are interconnected at various points to enhance fiber spreading.

FIG. 14 shows the catheter 1400 in its unretracted state. Many components of the catheter 1400 are similar to those discussed above, and are therefore omitted from the present discussion for ease of illustration. The inner tube 1402 resides within the outer tube 1403, and is slidably housed by a proximal fluid transfer housing 1404, but fixedly attached to a distal fluid transfer housing 1408. Numerous fibers 1404 of substantially equal length pass between the fluid transfer housings 1404/1408.

The fibers 1404 are attached at selected points 1450. These fibers may be attached by heat bonding, wrapping with a band, gluing, or another technique. One type of adhesive is UV adhesive, such as urethane acrylate. When a pulling force 1410 is applied to the inner tube 1402, withdrawal of the tube 1402 pulls the distal fluid transfer housing 1408 in the direction 1412. This causes the fibers 1404 to bow (not shown) between the fluid transfer housings 1404/1408. Moreover, the fibers' various interconnections cause the bundles of interconnected fibers to bow in various directions, further enhancing fiber spreading.

STAGGERED MULTI STAGE

Figure 15:
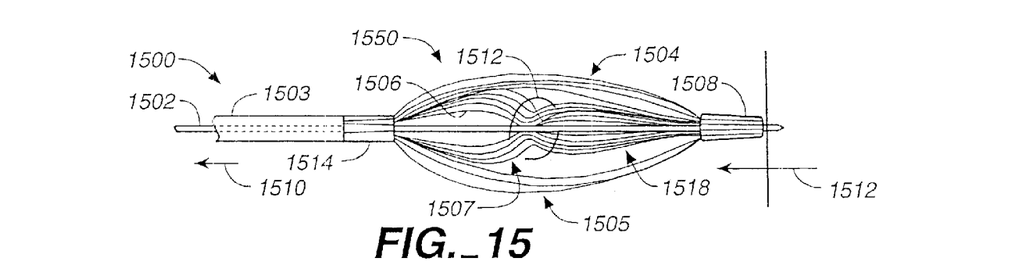
FIG. 15 is a plan view showing one of one catheter specific example exemplary a bound tip catheter with one exemplary embodiment a staggered-stage slidably retractable inner tube for spreading heat exchange fibers, shown in its retracted state, in accordance with the invention.

FIG. 15 shows a bound tip catheter 1500 that constitutes one particular example of the catheter 1400 (FIG. 14). FIG. 15 shows the catheter 1500 in its retracted state. Many components of the catheter 1500 are similar to those discussed above, and are therefore omitted from the present discussion for ease of illustration. The inner tube 1502 resides within the outer tube 1503, and is slidably housed by a proximal fluid transfer housing 1514, but fixedly attached to a distal fluid transfer housing 1508. Numerous fibers 1550 of substantially equal length pass between the fluid transfer housings 1514/1508.

There are various groups of fibers 1550 as discussed in greater below. The fibers 1550 include fiber groups 1506, 1507, 1504, 1505, and 1518. Certain of the groups are formed by connecting various fibers 1550, whereas other groups are defined by their lack of interconnection. Examples of interconnected fiber groups include the groups 1506, 1507, and 1518, which are defined by attaching the participant fibers at a region 1512 between the fluid transfer housings 1514/1508. These fibers may be attached by heat bonding, wrapping with a band, gluing, or another technique. One type of adhesive is UV adhesive, such as urethane acrylate. In contrast to the bound fibers 1506–1507, other groups 1504–1505 of fibers run freely from fluid transfer housing 1514 to fluid transfer housing 1508 without being connected to any other fiber. A variety of different fiber attachments are contemplated by the invention, the foregoing merely disclosing several examples.

When a pulling force 1510 is applied to the inner tube 1502, withdrawal of the tube 1502 pulls the distal fluid transfer housing 1508 in the direction 1512. This causes the free fibers 1550 to bow between the fluid transfer housings 1514/1508. The junction of fibers 1506 in the region 1502 causes them to bow differently. When retracted, then, the catheter thus provides a staggered multi stage bowed shape.

SHAPE MEMORY

If desired, the catheters of FIGS. 9–15 may be constructed with some or all fibers having shape memory, which further contributes to fiber spreading as discussed above.

RETRACTABLE SPREADING MEMBER

Figure 16:
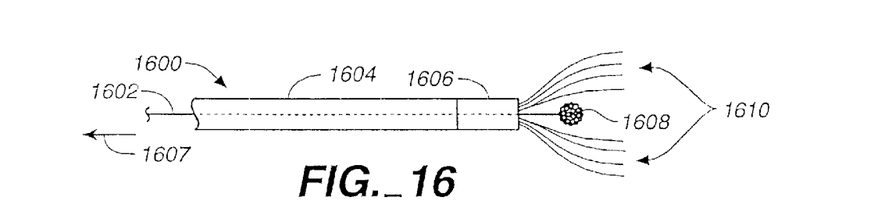
FIG. 16 is a plan view of a free tip catheter with a manually operated retractor for spreading heat exchange fibers, in accordance with the invention.

FIG. 16 shows a free tip catheter 1600 that uses a different spreading structure, exemplified by a retractable spreading member. Namely, the catheter 1600 includes a spreading member 1608 attached to a retraction line 1602 that passes through the outer tube 1604 and the fluid transfer housing 1606. The retraction line 1602 may pass through a tube (not shown) parallel to the inner tube (not shown), through the inner tube itself, or utilize another suitable configuration. In the illustrated example, the spreading member 1608 is a spherical ball made of polyurethane, polyolefin, polyether block amide, or steel, and having a diameter of about 3–8 millimeters.

When a pulling force 1607 is applied to the retraction line 1602, this pulls the spreading member 1608 toward the fluid transfer housing 1606. When the line 1602 is retracted sufficiently, the spreading member 1608 travels into the midst of the fibers 1610, causing the fibers 1610 to spread apart about the spreading member 1608.

Although a spherically shaped ball 1608 of a specific size is illustrated, ordinarily skilled artisans (having the benefit of this disclosure) will recognize that many different shapes and sizes of obstacle may be used, such as cubes, tetrahedrons, stars, cones, etc.

Externally Actuated: Spreading Balloon

Figure 17:
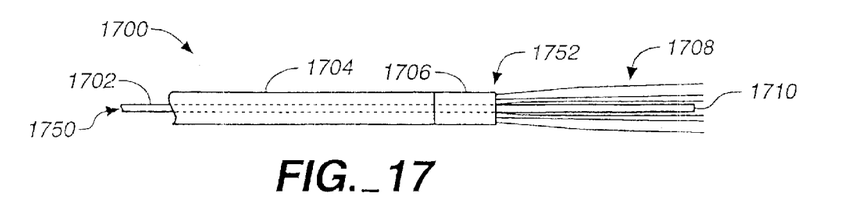
FIG. 17 is a plan view of a free tip catheter with a manually operated balloon for spreading heat exchange fibers, shown in its uninflated state, in accordance with the invention.

Another type of externally or "manually" actuated spreading structure is the spreading balloon, which is implemented in the free tip catheter 1700 of FIG. 17. The catheter 1700 includes a balloon 1710 coupled to an inflation line 1702. The balloon 1710, for example, may be constructed from urethane, an elastomeric material, or another suitably nonallergenic, flexible, and reliable substance. The inflation line 1702 passes through the outer tube 1704 and fluid transfer housing 1706 before reaching the balloon 1710. The line 1702 has a source end 1750 and a remote end 1752. In operation, the source end is coupled to a source of an inflation fluid, such as saline. The remote end 1752 is coupled to the balloon 1710; as an alternative, the remote end 1752 may be coupled to the fluid transfer housing 1706, which is in turn coupled to the balloon 1710.

Although omitted for clarity, the catheter 1700 also includes an inner tube that passes through the outer tube 1704 and fluid transfer housing 1706 to convey coolant to the fibers 1708, as in the previously explained free tip catheter embodiment 200 (FIG. 2).

Figure 18:
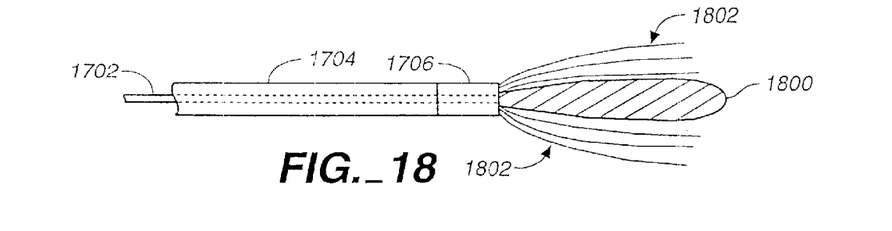
FIG. 18 is a plan view of the catheter of FIG. 17, with the balloon inflated, in accordance with the invention.

In its uninflated state, the balloon 1710 resides in the midst of the fibers 1708. To actuate the spreading balloon, an operator uses the inflation source (not shown) to direct an inflation fluid into the inflation line 1702, causing the balloon to inflate, as shown in FIG. 18. The source of inflation fluid may be provided by mechanized pump, hand pump, manually blowing air into the inflation line 1702, or any other suitable inflation means, including infusing the balloon with the coolant. As the balloon inflates, it emerges between the now spread-apart fibers 1802. After the fibers 1802 are spread, the balloon may be deflated, leaving the fibers 1802 free to stay apart or eventually come together, depending upon blood flow around the catheter 1700 and other influences.

The invention also includes many different embodiments achieved by modifying the spreading balloon or other features of the catheter 1700. For example, the spreading balloon may be similarly implemented (not shown) in a bound tip catheter, such as the catheter 100 (FIG. 10). The spreading balloon may also be implemented in a looped fiber catheter 300 (FIG. 3), for example by installing the balloon in an otherwise unoccupied region, such as a central position in the inner ring 376.

OPERATION

In addition to the various hardware embodiments described above, the invention also includes different method aspects, such as a techniques for manufacturing and using such catheters.

Using Catheters of This Invention

Figure 19:
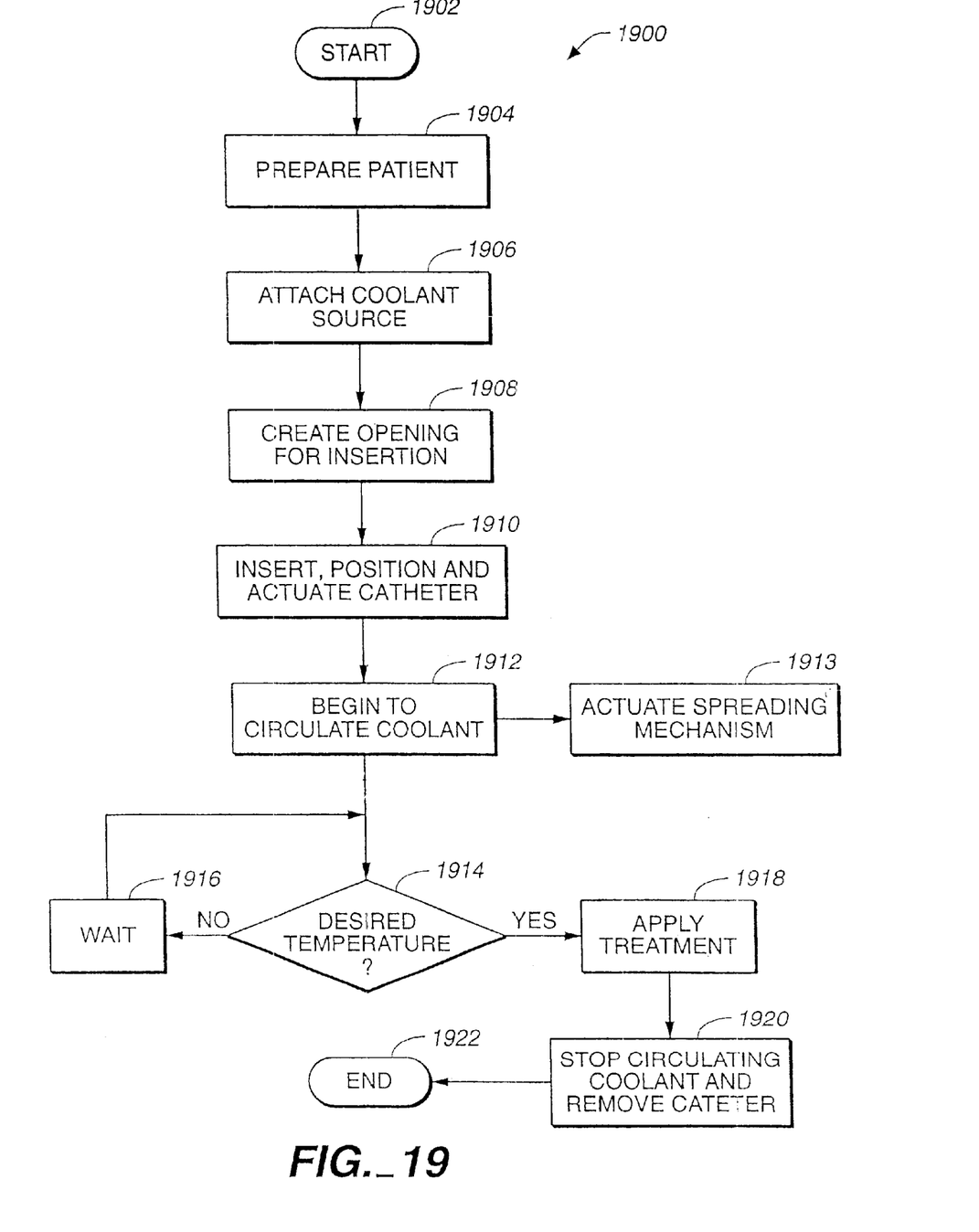
FIG. 19 a flowchart showing a sequence for using a catheter, in accordance with the invention.

FIG. 19 shows a sequence 1900 to illustrate a sequence of exemplary operations for utilizing a catheter of the invention to treat a patient. For ease of explanation, but without any intended limitation, the example of FIG. 19 is described in the context of the manually actuated catheter 900 (FIG. 9) described above. Step 1902 marks the beginning of the sequence 1900. In step 1904, physicians prepare the patient (not shown) for treatment. This may involve cleaning and disinfecting skin, removing hair, administering medicine, and other known procedures to ready the patient for surgery or other treatment.

In step 1906, physicians attach the catheter 900 to a coolant source (not shown). This source may include, for example, one or more syringes, pumps, gravity feed systems, or another appropriate device for circulating coolant through the catheter 100. One specific example is the Y-connector disclosed in the parent '0813 application. Although presently described in the context of a coolant, the coolant source may be a cooling fluid or a heating fluid, depending upon the particular application. In either case, heat exchange is occurring, and the heating/cooling fluid is nonetheless exemplified by "coolant." In many cases, a coolant may be especially useful to induce a controlled level of systemic hypothermia concurrent with surgery. The coolant comprises saline, carbon dioxide, or another hypoallergenic and inert substance that is safe for internal use in the body and will not cause any injury if it leaks from the catheter 900.

In step 1908, physicians prepare an existing body opening or create a new opening for insertion of the catheter 900. As an example of creating a new opening, doctors may cut an appropriately located incision or puncture in the groin, for insertion of the catheter into the femoral artery or vein. In step 1910, physicians insert the catheter 900 into the body opening, and feed the catheter in to a desired position. The catheter may be inserted through an introducer sheath (not shown), nozzle, tube, funnel, or another device designed to keep the fibers 914 together during insertion; this is especially beneficial for catheters with pre-shaped components or fibers that otherwise tend to spread apart. Also in step 1910, physicians activate the catheter 900 by withdrawing a length of the inner tube 904, thereby spreading the fibers 914 and actuating the catheter 900.

In step 1912, physicians begin to circulate the coolant to/from the catheter 900. In one embodiment, the coolant enters the inner tube 904, continues in the tube 904 through the fluid transfer housing 906, passes through the fluid transfer housing 908, changes course in the reservoir 909, and returns in the opposite direction through the fluid transfer housing 908, the fibers 914, the fluid transfer housing 906, and finally the passageway between the tubes 902/904. The coolant source cools (or heats) fluid received from the catheter 900, and redirects it into the inner tube 904. As the coolant passes through the catheter 900, and especially the heat exchange fibers 914, the coolant exchanges heat with the surrounding body fluid. In one embodiment, the surrounding body fluid is blood.

In step 1914, physicians determine whether the targeted body region has reached the desired temperature. This may involve measuring the temperature of a concentrated target region, or (in the case of systemic hypothermia) the body core temperature. If the target region has not reached the desired temperature, step 1916 waits and then returns to step 1914. During the wait step 1916, of course, physicians may perform other unrelated duties related to the treatment if desired. When the desired temperature is reached, the physicians treat the patient in step 1918. Treatment may involve surgery, or another medical procedure that benefits by induced hypothermia or hyperthermia. After the treatment of step 1918 is complete, physicians stop circulating the heat exchange fluid and remove the catheter in step 1920. Alternatively, depending upon the treatment being performed, physicians may decide to continue operating the catheter 900 for some time after treatment ends. For example, the patient can be re-warmed in a controlled manner after therapeutic hypothermia by using the body core temperature as a feedback signal to the control unit, to cause less-cool or possibly warm (>38° Celsius) saline to flow through the catheter. In re-warming the patient, the system monitors the rate of warm-up rate to avoid re-warming too rapidly or too slowly.

Also as part of step 1920, the patient's incision (if any) is closed and any other applicable post treatment procedures are performed. The sequence ends in step 1922.

An Exemplary Manufacturing Technique

Figure 20A:
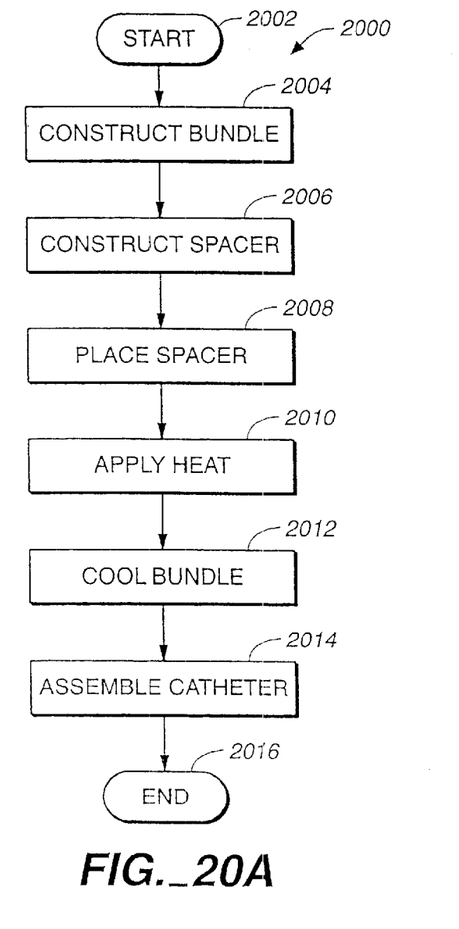
FIG. 20A is a flowchart showing a sequence for manufacturing a catheter, in accordance with the invention.
Figure 20B:
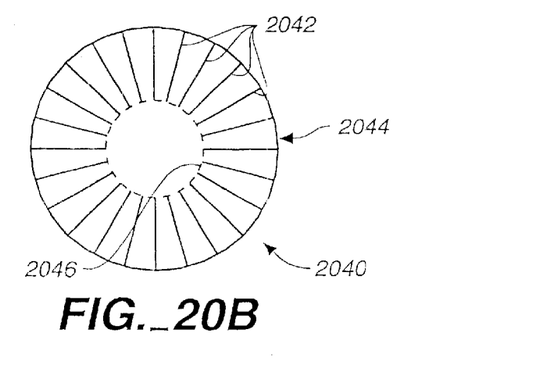
FIG. 20B is a perspective view of a spacer for use in constructing a bound tip catheter with fiber pre-shaping, in accordance with the invention.
Figure 20C:
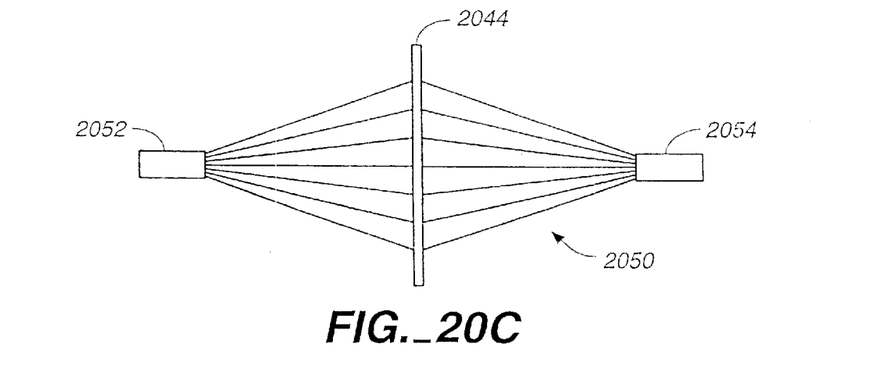
FIG. 20C is a plan view of a fiber bundle with fibers held in position by the spacer of FIG. 20B, in accordance with the invention.

FIG. 20A shows a sequence 2000 of exemplary operations for constructing a bound tip catheter equipped with pre-shaping. For ease of explanation, but without any intended limitation, the example of FIG. 20A is described in the context of the catheter 500 (FIG. 5) described above. FIGS. 20B–20C show some exemplary hardware components involved in the construction of the catheter 500. Step 2002 marks the beginning of the sequence 2000. In step 2004, technicians construct a fiber bundle, including the first 2052 and second 2054 fluid transfer housings, interconnected by fibers 2050 (FIG. 20C). The parent' 813 application describes fiber bundle construction in greater detail.

In step 2006, technicians create a spacer 2040 (FIG. 20B). As illustrated below, the spacer 2040 is used to introduce a desired outward curve in the fibers 2050. In this particular example, which pertains to a specific desired shape, the spacer 2040 comprises a disk 2044. The disk 2044 includes a number of slits 2042, which may be made by cutting with a blade, trimming with a laser, being defined as an inherent part of a vacuum mold, etc. The number of slits is the same or more than the number of fibers 2050. The slits 2042 extend into the disk 2044 a fixed distance, in effect creating a circular central hub 2046. This hub, for example, may have a diameter of about two inches. This completes construction of the spacer 2040 (step 2006).

After step 2006, technicians place the spacer 2040 between the fibers 2050, and individually slide each fiber 2050 all the way down into a corresponding slit 2042. The fibers are distributed evenly around central hub 2046. With the fibers held in this position by the spacer 2040, step 2010 heats the bundle and spacer to establish a default shape memory. As an example, step 2010 may involve placing the fiber bundle and spacer into an industrial oven (not shown) and heating at 1800 Fahrenheit for one hour.

After step 2010, the bundle is cooled. One exemplary cooling technique involves immersing the bundle and spacer in cold water. The fiber bundle is immersed while the bundle cools sufficiently for the fibers to adopt, as a default shape, the bowed shape held by the spacer 2040 during heating. After cooling of the bundle, the spacer 2040 is removed from the now-shaped fibers and the bundle is integrated with the remaining components of the catheter in a final assembly (step 2014). After step 2014, the sequence 200 ends in step 2016.

OTHER EMBODIMENTS

While the foregoing disclosure shows a number of illustrative embodiments of the invention, it will be apparent to those skilled in the art that various changes and modifications can be made herein without departing from the scope of the invention as defined by the appended claims. Furthermore, although elements of the invention may be described or claimed in the singular, the plural is contemplated unless limitation to the singular is explicitly stated.

Moreover, the present invention is presently described in the context of the human body merely for ease of illustration, without any intended limitation. The invention may also be practiced with other beings, such as mammals, birds, reptiles, or other creatures. Furthermore, although the foregoing discussion has described catheter use to induce a hypothermic state, ordinarily skilled artisans (having the benefit of this disclosure) will recognize that the invention also contemplates the use of catheters to induce systemic or local hyperthermia. In addition, although each conceivable example has not been specifically illustrated, a nearly endless number of permutations are possible by combining various features disclosed herein, such as pre-shaping or shape memory, externally operated actuating structures, spiraling, etc.

Additionally, although certain fluid flow paths have been specifically illustrated for ease of understanding, opposite direction flow paths may be used instead. In such alternatives, references to "supply" or "return" conduits or ends are accordingly reversed.

What is claimed is:

1. A heat exchange catheter, comprising:
   first and second fluid conduits each having a proximal and a distal end;
   multiple hollow fibers of substantially equal length, the fibers having substantially coterminous proximal and distal ends, each hollow fiber forming a sealed fluid path;

a proximal fluid transfer housing forming a sealed fluid path between the fibers' proximal ends and the first conduit;

a distal fluid transfer housing forming a sealed fluid path between the fibers' distal ends and the second conduit; and an actuating structure to spread the fibers under predetermined conditions.

2. The catheter of claim 1, the distal fluid transfer housing including a distally positioned fluid reservoir, where the distal fluid transfer housing forms a sealed path between the fibers' distal ends and the second conduit via the fluid reservoir.

3. The catheter of claim 1, the catheter including an outer tube and an inner tube, the outer tube surrounding the inner tube, where the inner tube provides the second fluid conduit and proceeds from the proximal fluid transfer housing to the distal fluid transfer housing in parallel along with the fibers, and a passageway between the inner and outer tubes provides the first fluid conduit.

4. The catheter of claim 3, the actuating structure comprising:

a coupling between the proximal fluid transfer housing and the inner tube being such that the proximal fluid transfer housing surrounds the inner tube while leaving the inner tube free to slide toward and away from the distal end, the coupling permitting the inner tube to be slidably withdrawn causing withdrawal of the distal fluid transfer housing and the fibers' distal ends and consequently spreading the fibers.

5. The catheter of claim 1, where each fiber has an outer diameter of about 0.020–0.024 inches and an inner diameter of about 0.016–0.0195 inches.

6. The catheter of claim 5, where each fiber has an outer diameter of about 0.022 inches and an inner diameter of about 0.0185 inches.

7. A heat exchange catheter, comprising:

a first fluid conduit having a proximal end and a distal end;

a second fluid conduit having a proximal end and a distal end;

multiple hollow fibers having substantially coterminous proximal and distal ends, each fiber defining a sealed fluid pathway between the proximal end and the distal end of each fiber, each fiber being sealed such that neither liquid nor air may pass through the fiber other than through the pathway;

a proximal fluid transfer housing sealingly engaging, and forming a sealed fluid path between, the fibers' proximal ends and the first fluid conduit;

a distal fluid transfer housing sealingly engaging, and forming a sealed fluid path between, the fibers' distal ends and the second fluid conduit; and an actuating structure wherein the actuating structure comprises an inner tube and an outer tube with the inner tube being slideable within the outer tube, sliding of the inner tube within the outer tube encouraging spreading of the fibers.

8. The catheter of claim 7, the distal fluid transfer housing including a distally positioned fluid reservoir forming at least part of the sealed fluid path between the fibers' distal ends and the second fluid conduit.

9. The catheter of claim 7 wherein the inner tube extends from the proximal fluid transfer housing to the distal fluid transfer housing with at least a portion of the second fluid conduit being disposed in the inner tube; and the outer tube at least partially surrounds the inner tube with at least a portion of the first fluid conduit being disposed between the outer tube and the inner tube.

10. The catheter of claim 9, the inner tube having a shape such that the inner tube contacts and tends to spread the fibers apart in the absence of straightening forces acting on the inner tube.

11. The catheter of claim 7, the fibers having pre-formed shapes and being connected with the proximal and distal fluid transfer housings such that internal forces within the fibers together with external forces exerted by the proximal and distal fluid transfer housings tend to spread the fibers apart.

12. The catheter of claim 11, the shape of each fiber being at least partially dependent on the temperature of each fiber.

13. The catheter of claim 7, each fiber having an outer diameter of about 0.020 to about 0.024 inches and an inner diameter of about 0.016 to about 0.0195 inches.

14. The catheter of claim 13, each fiber having an outer diameter of about 0.022 inches and an inner diameter of about 0.0185 inches.

* * * * *